United States Patent [19]
Drope

[11] Patent Number: 5,144,832
[45] Date of Patent: Sep. 8, 1992

[54] FLOW CHARACTERIZATION APPARATUS AND PROCESS

[75] Inventor: David L. Drope, Petrolia, Canada

[73] Assignee: Polysar Rubber Corporation, Sarnia, Canada

[21] Appl. No.: 674,156

[22] Filed: Mar. 25, 1991

[51] Int. Cl.$^5$ .............................................. G01N 11/12
[52] U.S. Cl. .................................................. 73/54.15
[58] Field of Search ................................................ 73/57

[56] References Cited

U.S. PATENT DOCUMENTS

| | | | |
|---|---|---|---|
| 1,062,032 | 5/1913 | Rawstron | 73/57 |
| 1,225,438 | 5/1917 | Howard | 73/57 |
| 1,565,502 | 12/1925 | Rodler | 73/57 |
| 1,748,513 | 2/1930 | Knopf | 73/57 |
| 2,638,779 | 5/1953 | Wilson | 73/57 |
| 2,913,898 | 11/1959 | O'Halloran et al. | 73/57 |
| 3,706,221 | 12/1972 | Fletcher et al. | 73/57 |

FOREIGN PATENT DOCUMENTS

| | | | |
|---|---|---|---|
| 147883 | 11/1954 | Sweden | 73/57 |
| 751958 | 7/1956 | United Kingdom | 73/57 |

Primary Examiner—Hezron E. Williams
Assistant Examiner—Joseph W. Roskos
Attorney, Agent, or Firm—Stevens, Davis, Miller & Mosher

[57] ABSTRACT

There is provided an apparatus, and a process using the apparatus, for determining the flow characteristics of a synthetic rubbery polymer in which the vertical displacement is measured of a contact rod which is in contact with a disc contacting a sample of said polymer located between said disc and a base plate.

5 Claims, 1 Drawing Sheet

FLOW CHARACTERIZATION APPARATUS AND PROCESS

FIELD OF THE INVENTION

The invention is directed to an apparatus and a process using such apparatus for the determination of the flow characteristics of synthetic rubbery polymers.

BACKGROUND OF THE INVENTION

The flow characteristics of synthetic rubbery polymers are important for a variety of reasons including the ability to mold by injection such polymers and the distortion of packages of such polymers. Of primary, but not the only, concern in the present injection is the flow of polymers during storage in packages, commonly referred to as cold flow. If a polymer has a high tendency to cold flow the package containing such a polymer will become distorted over time causing the handling of such a package to be difficult. If there is a desire to fracture bales of polymer into small particles, those polymers having a high tendency to cold flow are more difficult to handle.

Accordingly, there is a need to be able to readily determine the flow characteristics of synthetic rubbery polymers. In the past this has been achieved by the very simple method of placing a cube or a plug of the polymer on a surface which is inclined at 30° or 40° to the horizontal and measuring the extent of flow down the surface. The method using the apparatus of this invention is faster, easier, more controllable, more accurate and readily reproducible.

SUMMARY OF THE INVENTION

There is provided an apparatus for the determination of the flow characteristics of a synthetic rubbery polymer which comprises a base plate, attached to said base plate a vertical retaining rod, a vertical guide of shorter length than said vertical retaining rod and having a centrally located full length aperature, at least two spaced apart horizontal support rods each attached at one end to said vertical retaining rod and at the opposite end to said vertical guide, located within the aperture of said vertical guide a vertical contact rod which is freely moveable in the vertical direction within said vertical guide and extends in the upward and downward directions above and below said vertical guide, a bottom plate located at and having its uppermost surface in contact with the lowermost end of said vertical contact rod, a disc located at and in contact with the uppermost end of said vertical contact rod and being removeable and replaceable to provide the weight required for the particular synthetic polymer being tested, a horizontal holding rod attached at one end to an uppermost point of said vertical retaining rod, a micrometer having a contact point for sensing vertical displacement and being attached to the opposite end of said horizontal holding rod, the contact point of said micrometer being in direct contact with said disc to sense the vertical displacement of said disc, the lowermost surface of said bottom plate being in close proximity to the uppermost surface of said base plate, said bottom plate being vertically displaceable from said base plate such that a sample of the synthetic polymer to be tested can be located between and in contact with the lowermost surface of said bottom plate and the uppermost surface of said base plate.

There is also provided a process for measuring the flow characteristics of a synthetic rubbery polymer using the apparatus as described hereinbefore wherein a sample of polymer having a thickness of from about 5 to about 25 mm is located between said bottom plate and said base plate and the vertical displacement of said vertical contact rod is measured over a time period of from about 5 minutes to about 24 hours.

DETAILED DESCRIPTION OF THE INVENTION

Figure 1:
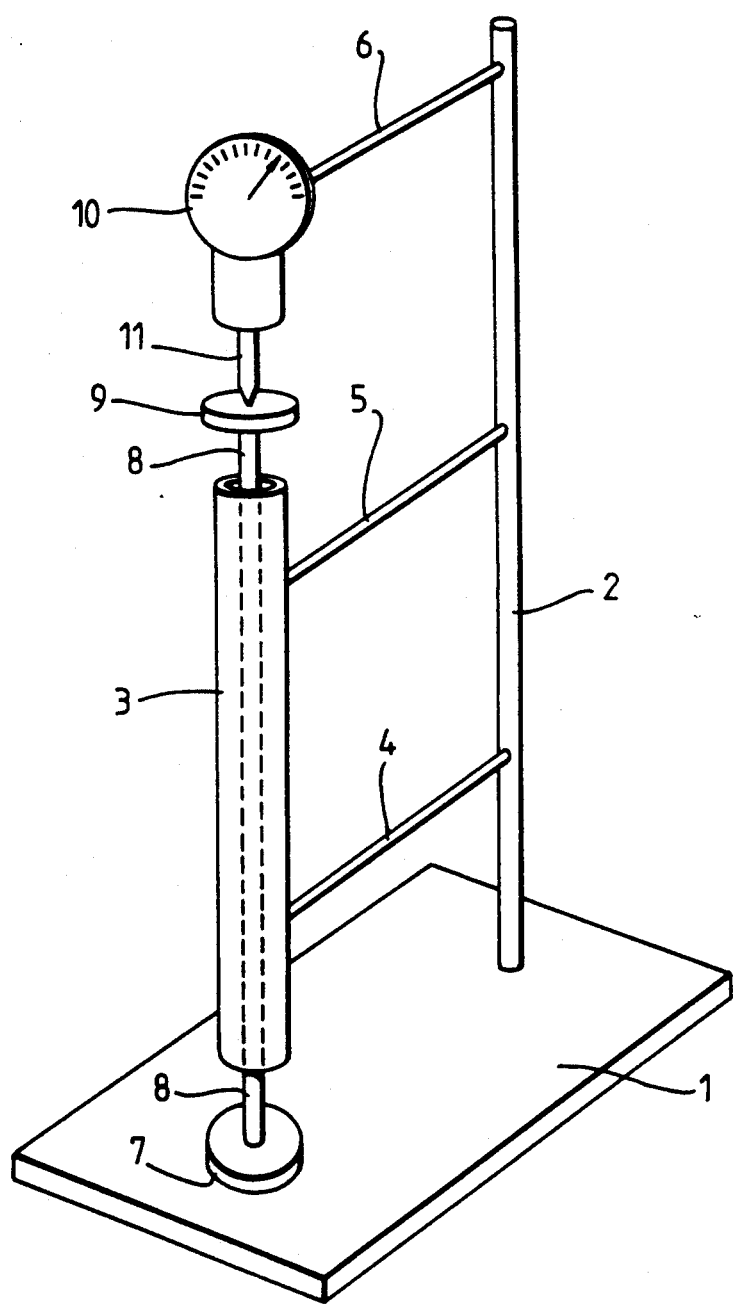
FIG. 1 is a schematic drawing of an apparatus in accordance with the invention.

With reference to FIG. 1, the base plate 1 is suitably a plate of metal having a thickness of from about 3 to about 15 mm thickness and being of a suitable size for the apparatus typically from about 10 cm by about 20 cm to about 20 cm by about 40 cm. The vertical retaining rod 2 is suitably a metal rod of approximately circular dimension typically with a diameter of from about 5 to about 12 mm and a length of from about 60 to about 90 cm. The vertical guide 3 is suitably a metal pipe having a diameter of from about 1.2 to about 2 cm and length from about 35 to about 45 cm and having an aperture of circular form and diameter of from about 4 to about 7 mm running the full length of the guide. The horizontal support rods 4 and 5 are suitably of square or circular cross section having a thickness of from about 5 to about 10 mm and are firmly attached at their ends to each of the vertical retaining rod and the vertical guide. Typically support rod 4 is located about 10 to about 20 cm above the base plate and support rod 5 is located about 30 to about 50 cm above the base plate. The horizontal holding rod 6 is suitably of square or circular cross section having a thickness of from about 5 to about 10 mm and is firmly attached to the vertical retaining rod and firmly though replaceably attached to the micrometer 10. The horizontal holding rod typically is located about 50 to about 80 cm above the base plate. The vertical contact rod 8 is a smooth surface circular cross section rod having a diameter of from about 3.5 to about 6.5 mm—the length of this rod is appropriate to the length of the vertical guide and typically is from about 40 to about 60 cm long. The bottom plate 7 is preferably a circular metal plate typically having a diameter of from about 4 to about 7.5 cm and a thickness of about 2.5 to about 5 mm. Disc 9 is preferably a circular metal plate typically having a diameter of from about 4 to about 7.5 cm and a thickness of from about 2 to about 7 mm. Disc 9 is removeable so that it can be replaced with other discs of varying thickness in order that the force applied in the downward direction to the vertical contact rod may be varied, in essence by adjusting the weight of the disc. Such variation is desirable in order that polymers having different flow characteristics can be tested within a reasonable test time. The micrometer 10 can be any of the known units which measure vertical displacement. The micrometer is equipped with a contact point 11 which is in direct contact with disc 9 and sense the vertical displacement of the disc, this vertical displacement then being measured and recorded by the micrometer. The micrometer may be equipped with a readable dial which directly shows the vertical displacement of the contact point 11 or may be equipped to provide the vertical displacement to a recorder such as an electronic means or a computer programmed to record the reading at set time intervals. For greatest accuracy and efficiency, a recorder is preferred especially a computer so that once the test is initiated no further manpower is required and the results may be automatically recorded and even displayed on a screen. A person of average skill in the art can readily assemble such a recorder. If the micrometer is equipped with a readable dial it is necessary to have the readings taken at specified time intervals and manually recorded.

In a process for determining the flow characteristics of a polymer using the apparatus as hereinbefore described, a sample of the polymer is formed such that it has a thickness of from about 5 to about 25 mm, preferably from about 7 to about 15 mm, and is placed between the bottom plate and the base plate. The forming of such a sample can be by cutting out from a sheet or by removal of a plug from a large sample or by similar appropriate means. Typically the sample would be or circular form with a diameter of from about 5 to about 30 mm, preferably from about 7 to about 15 mm. The reading on the micrometer would be either read or recorded as that at zero time and the vertical displacement of the vertical contact rod would then be measured with time. The time over which readings would be taken is from about 5 minutes to about 24 hours, preferably from about 5 minutes to 2 hours and most preferably from about 5 to about 30 minutes. Limited experimentation may be necessary to determine the desired weight of disc 9 to achieve such times—typically the weight of the disc will be from about 50 to about 500 g, preferably from about 75 to about 400 g. If the time over which measurements are taken is less than about 5 minutes accuracy of measurement and reproducibility diminish whereas if the time is greater than 24 hours the data may not be available in the time frame necessary. It is desirable that the vertical displacement not be too great—typically vertical displacements, depending on the original thickness of the sample, of from about 2.5 to about 12.5 mm are desirable, preferably from about 5 to about 7.5 mm. The vertical displacement with time is recorded, manually or electronically, and is then plotted as displacement versus time. The actual displacement at one or more set times, for example at 5, 10 and/or 15 minutes, describe the flow characteristics of that polymer and may be compared with those of other similar polymers. The process of this invention is used to measure the flow characteristics of synthetic rubbery polymers such as butyl rubber, EPDM and polybutadiene, especially polybutadiene, the measurements being taken at room temperature and over a time of from about 5 to about 30 minutes. The results may be used to compare samples of polybutadiene and may be useful as tools for monitoring the quality of the polybutadiene.

What is claimed is:

1. An apparatus for the determination of the flow characteristics of a synthetic rubbery polymer which comprises
   a base plate,
   attached to said base plate a vertical retaining rod,
   a vertical guide of shorter length than said vertical retaining rod and having a centrally located full length aperature,
   at least two spaced apart horizontal support rods each attached at one end to said vertical retaining rod and at the opposite end to said vertical guide,
   located within the aperture of said vertical guide a vertical contact rod which is freely moveable in the vertical direction within said vertical guide and extends in the upward and downward directions above and below said vertical guide,
   a bottom plate located at and having its uppermost surface in contact with the lowermost end of said vertical contact rod,
   a disc located at and in contact with the uppermost end of said vertical contact rod and being removeable and replaceable to provide the weight required for the particular synthetic polymer being tested,
   a horizontal holding rod attached at one end to an uppermost point of said vertical retaining rod,
   a micrometer having a contact point for sensing vertical displacement and being attached to the opposite end of said horizontal holding rod,
   the contact point of said micrometer being in direct contact with said disc to sense the vertical displacement of said disc,
   the lowermost surface of said bottom plate being in close proximity to the uppermost surface of said base plate, said bottom plate being vertically displaceable from said base plate such that a sample of the synthetic polymer to be tested can be located between and in contact with the lowermost surface of said bottom plate and the uppermost surface of said base plate.

2. The apparatus of claim 1 wherein said micrometer is equipped with a readable dial.

3. A process for measuring the flow characteristics of a synthetic rubbery polymer using the apparatus of claim 1 wherein a sample of polymer having a thickness of from about 5 to about 25 mm is located between said bottom plate and said base plate and the vertical displacement of said vertical contact rod is measured over a time period of from about 5 minutes to about 24 hours.

4. The process of claim 3 wherein the flow characteristics are measured at room temperature.

5. The process of claim 4 wherein the synthetic polymer is polybutadiene and the vertical displacement of said vertical contact rod is measured over a time period of from about 5 to about 30 minutes.

* * * * *